United States Patent
Chagnot

(10) Patent No.: US 8,138,446 B2
(45) Date of Patent: Mar. 20, 2012

(54) MONITORING METHOD AND DEVICE BY SHADOWSCOPY

(75) Inventor: Christophe Chagnot, Velizy (FR)

(73) Assignees: Commissariat a l'Energie Atomique (FR); Compagnie Generale des Matieres Nucleaires (FR)

(*) Notice: Subject to any disclaimer, the term of this patent is extended or adjusted under 35 U.S.C. 154(b) by 924 days.

(21) Appl. No.: 10/589,797

(22) PCT Filed: Feb. 21, 2005

(86) PCT No.: PCT/FR2005/050107
§ 371 (c)(1),
(2), (4) Date: Jul. 23, 2008

(87) PCT Pub. No.: WO2005/085814
PCT Pub. Date: Sep. 15, 2005

(65) Prior Publication Data
US 2008/0283510 A1   Nov. 20, 2008

(30) Foreign Application Priority Data

Feb. 23, 2004 (FR) ...................... 04 50331

(51) Int. Cl.
*B23K 37/04* (2006.01)
*G01B 5/00* (2006.01)
(52) U.S. Cl. .......... 219/121.63; 219/121.64; 219/121.82
(58) Field of Classification Search ............. 219/121.63, 219/121.64, 121.83, 121.78, 121.81, 121.82, 219/121.85, 121.6; 356/602
See application file for complete search history.

(56) References Cited

U.S. PATENT DOCUMENTS

| 2,349,429 | A | * | 5/1944 | Herzog et al. | 378/54 |
| 4,453,410 | A | * | 6/1984 | Schmitz et al. | 73/640 |
| 4,561,062 | A | * | 12/1985 | Mitchell | 702/40 |
| 4,634,879 | A | * | 1/1987 | Penney | 250/559.22 |
| 4,695,729 | A | * | 9/1987 | Monno et al. | 250/358.1 |
| 4,831,232 | A | * | 5/1989 | Andersson et al. | 219/124.34 |
| 5,388,129 | A | * | 2/1995 | Hartley | 376/249 |
| 6,023,044 | A | * | 2/2000 | Kosaka et al. | 219/124.34 |

FOREIGN PATENT DOCUMENTS

| JP | 53115640 | A | * | 10/1978 |
| JP | 54100948 | A | * | 8/1979 |
| JP | 59120390 | A | * | 7/1984 |
| JP | 10288588 | | | 10/1998 |

OTHER PUBLICATIONS

Chagnot, et al "Vision De La Scene De Soudage Et traitement D'Image En Soudage Tig", XP-000779969, vol. 52, No. 5/6 of May 1, 1998, pp. 3-7.
Allemand, et al. "A Method Of Filming Metal Transfer In Welding Arcs", XP-009031097, Welding Journal, Jan. 1985, pp. 45-47.
International Search Report ISA 210 citing above references.

* cited by examiner

*Primary Examiner* — Samuel M Heinrich
(74) *Attorney, Agent, or Firm* — Baker + Hostetler LLP

(57) ABSTRACT

A monitoring device by laser shadowscopy, which comprises a light emitter (5) and receiver (6), mounted on an arm (8) oscillating at will around two joints (13, 14), in order to restore the image of the monitored profile more accurately. An important application relates to welding methods and especially in hollow beveled edges.

12 Claims, 3 Drawing Sheets

MONITORING METHOD AND DEVICE BY SHADOWSCOPY

Figure 1:
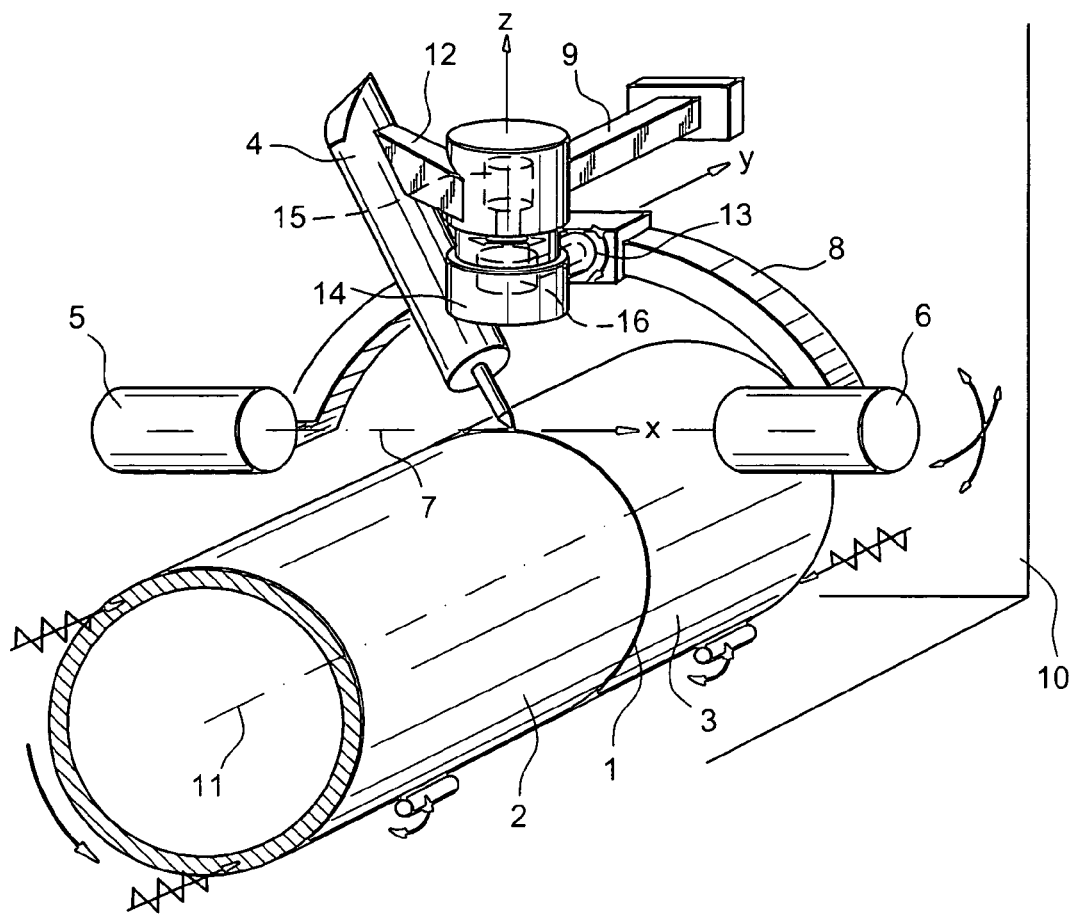

The field of this invention is monitoring in metrology, and its subjects are a shadowscopy method and device which may be applied to connections of parts, for example tubes placed end-to-end. Other applications are quite possible.

The undertaken monitoring operations may precede a machining operation and have the purpose of checking the positions of the observed parts, or be undertaken during the operation in order to check the proper position of the tool and the quality of the operation, for example from the aspect of a weld bead.

A known technique for metrological monitoring of a surface without any material contact with the latter consists of projecting a plane laser beam towards the surface and reading the position of the intersection line from the one which is collected on the image of a camera. This very widespread method is however subject to a few limitations, notably to the welding methods where significant light is produced by the molten bath, which may make that of the laser indistinct. Difficulties further appear for reading recessed surfaces, because of reflections between the walls and density variations of reflected rays.

Another technique consists of abandoning independent lighting of the scene to be monitored and of using the light produced by the molten bath for recognizing the image of the scene. It is obviously limited to welding methods. The quality of the results depends on the nature of the parts and of the parameters of method, which should also remain relatively constant. Selecting the conditions of observation is often delicate or even impossible to obtain good results. In both of these known techniques, the drawback is the too intense light produced by the molten bath, but especially by the plasma (or the flame) induced by the method, or even produced by the tools brought to a high temperature by the heat source: for example, the tip of the electrode for the TIG (tungsten inert gas) welding method, the end of the meltable wire or of the rod for MIG (metal inert gas) methods, MAG (metal active gas) methods, or the coated electrode as well as the red-hot ceramic nozzles providing an inflow of protective gas).

The invention belongs to another technique, so-called shadowscopy, where independent lighting of the monitored scene is provided and where the relief of the observed scene is inferred from the shadows produced by the independent light on the image recorded by the camera. The light is then projected in a direction substantially tangent to the surface to be monitored. This technique may be applied to the observation of opaque objects surrounded with a very luminous source, as in the arc plasma which blinds the detectors and prevents direct observation. In the case of welding methods, methods for reloading filler material of a welded joint and for cutting, the method will notably allow recognition of the shapes and positions of the parts at their junction, of the position of the tool, the aspect of the weld bead and notably the amount of deposited material, the quality of the wetting, the regularity and features of material deposition (side position, penetration angle, dimension and frequency of the drops, etc.). Corrections may be made to the method as soon as defects will have been noticed.

The foundations of shadowscopy are described in a German article, published in the "Welding Journal" of January 1985 and entitled <<A method of filming metal transfer in welding arcs>>.

One aspect of the invention will be to create a shadowscopy device with a laser or another source of light, such as a light-emitting diode, which may be used under particular assembling conditions and notably for capturing pronounced hollow relief features, under welding conditions in a beveled edge, for example.

A general form of the monitoring device comprises a support, a light source, a receiver for the light of the source, characterized in that it further comprises an arm with two opposite ends on which the source and the receiver are mounted, and a double and adjustable joint through which the arm is mounted on the support, the double joint comprising two axes of rotation substantially perpendicular to each other and with a main path of the light between the source and the receiver. It will be seen that this arrangement lends itself to convenient monitoring operations of surfaces in relief.

A tool-supporting member carrying out an operation monitored by this device, may be mounted on the support. The tool then accompanies the monitoring device, which is appropriate in many methods.

The arm may be curved between the ends, so as to properly clear the scene to be observed, and the source and the receiver may be provided with right-angle reflecting devices for the light and positioned parallel to each other, and perpendicularly to the main path of the light, which reduces the bulkiness of the device. Another kind of improvement which may be made to the device, would consist in that, as the light is monochromatic, the receiver would comprise a filter transparent to the light and opaque at other optical wavelengths, a converging lens, and pinhole placed at one focus of the light, created by the lens. Both a band-pass filter and a special filter would be formed, the common advantage of which would be to blot out the influence of the ambient light, for example produced by the molten bath.

Another aspect of the invention is a method for monitoring a scene, carried out with the previous device; it consists of placing the device so that the main path of the light is tangent to the scene to be monitored, and of adjusting the arm in orientation by adjustments of the double joint. Apprehension of the relief features is in fact distorted by bad orientation of the shadowscopy device; the invention lends itself to easy corrections of this orientation, from simple criteria, examples of which will be given later on.

An important application relates to circular junctions, notably in relief, of aligned tubes, the tubes being orientated parallel to a first of the axes of rotation; frequently, the tubes are rotary in front of the device and the arm is subject to an oscillatory rotation at least around the first of the axes of rotation, in order to track the bottom of the relief properly. But the device may also rotate around fixed tubes.

Figure 3:
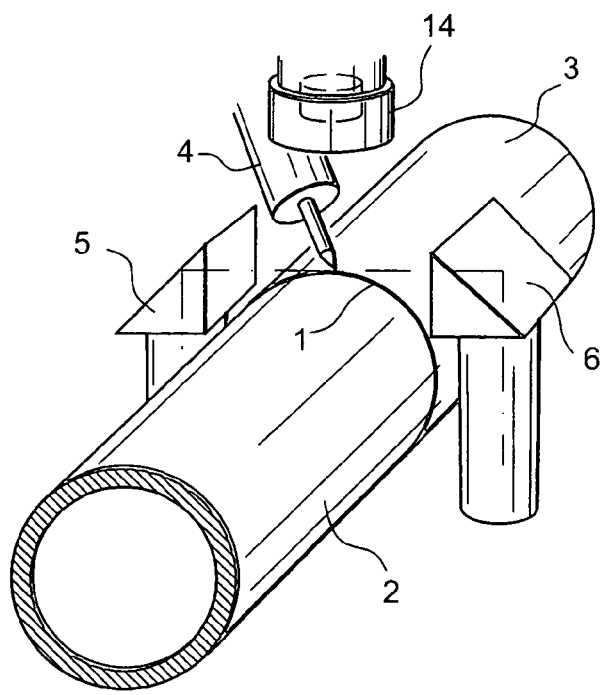
Figure 2:
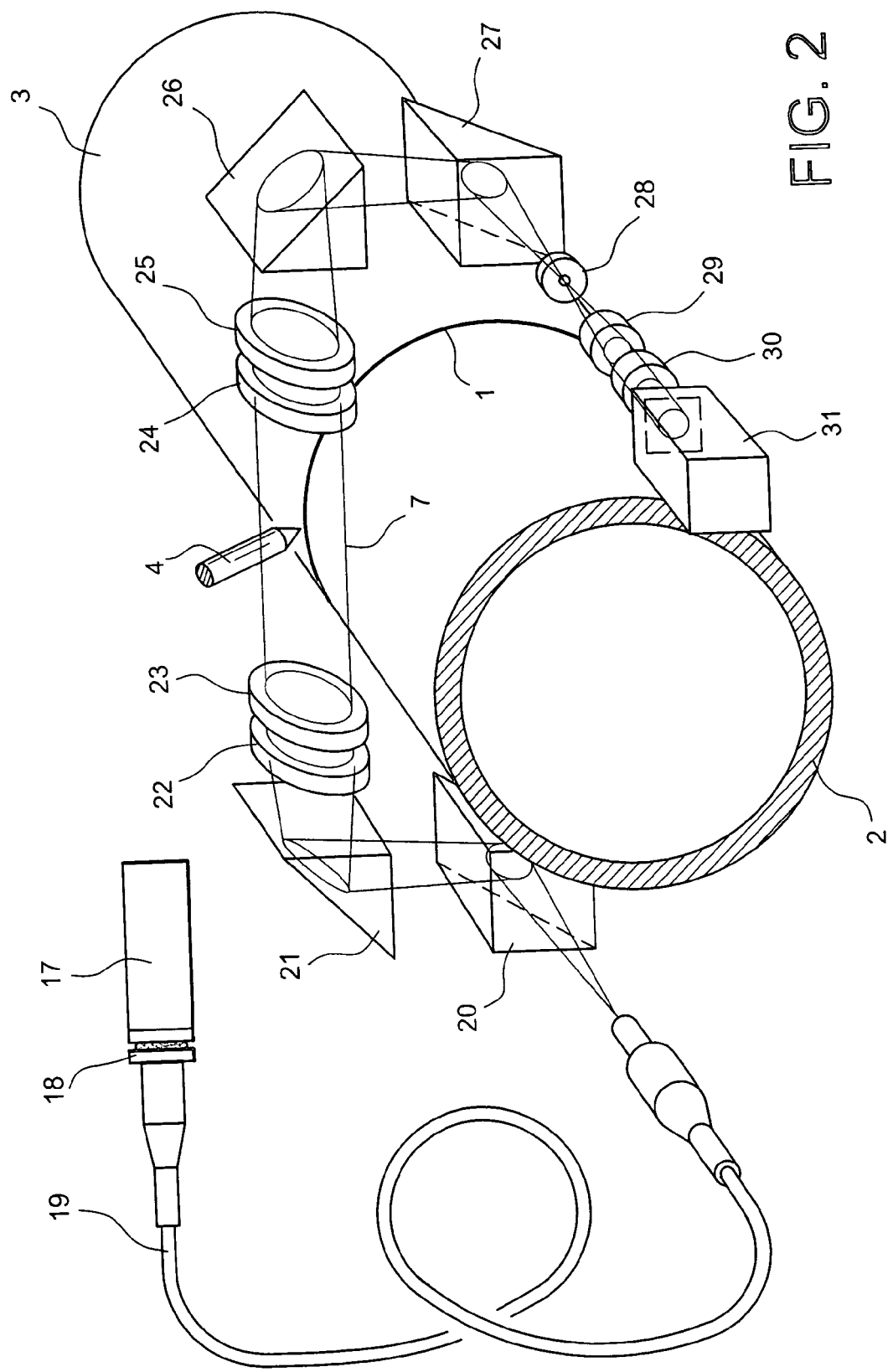
Figure 4:
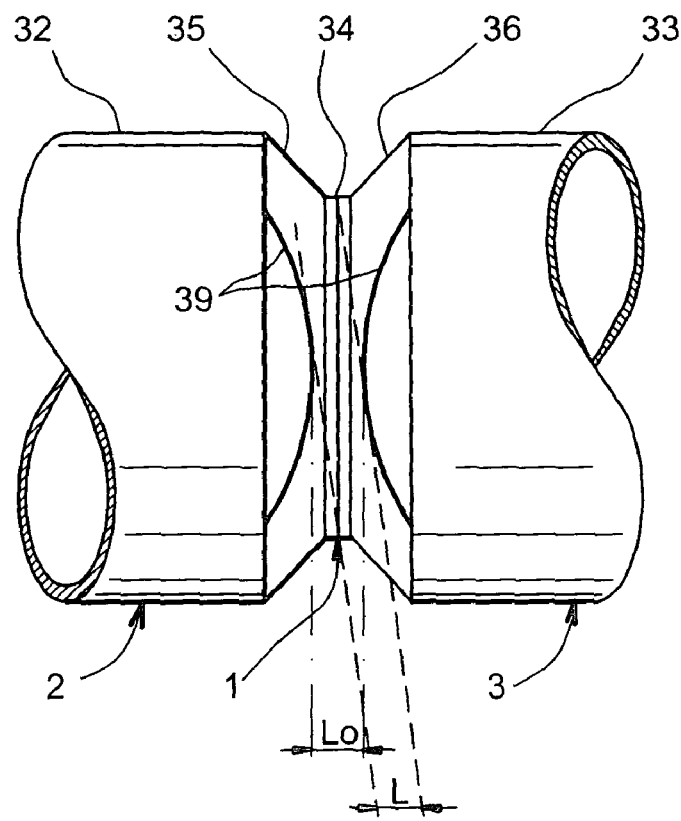
Figure 5:
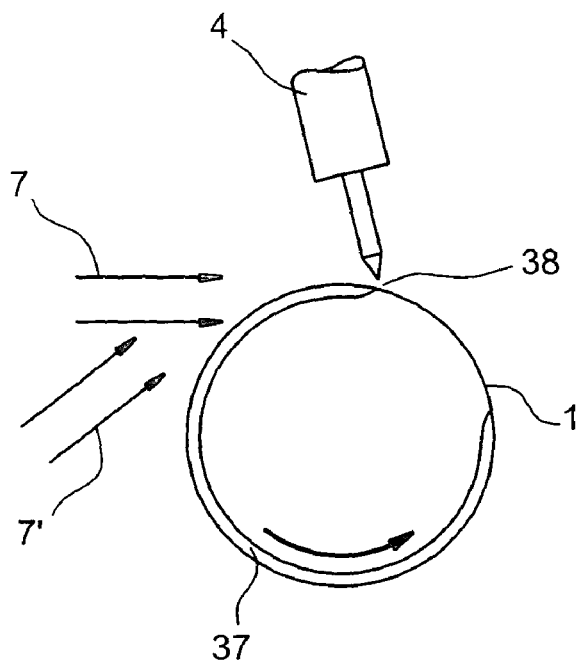

The invention will now be described in connection with the figures:

FIG. 1 is a general view of the device,
FIG. 2 is a detailed illustration of the optical system,
FIG. 3 is an alternative embodiment,
FIG. 4 and FIG. 5 illustrate applications of measurements by the device.

The device illustrated in FIG. 1 is intended to monitor the connection 1 as a circular line, of two tubes 2 and 3 joined end-to-end. The connection 1 is intended to be welded with a tool 4 accomplishing any welding method. The monitoring device which is relevant here, comprises a light emitter 5 and a receiver 6 for this same light, aligned along a main path 7 of the light substantially tangent to the tubes 2 and 3 and illuminating the region of the connection 1 on which the tool 4 operates, and which are supported at the ends of a curved arm 8 passing above the tubes 2 and 3. The arm 8 is supported by a supporting member 9 attached to a welding facility 10 not illustrated in detail and which also comprises means, which are not further illustrated, for maintaining the tubes 2 and 3 in abutment, while letting them rotate around their axis 11. The tool 4 is connected to the supporting member 9 by a stiff connecting support 12 and the arm 8 is connected to the supporting member 9 through a double joint consisting of a first joint 13 with an axis y parallel to the axis 11 of the tubes 2 and 3, and of a second joint 14, the axis z of which is directed towards the connection 1. Both of these joint axes are both either perpendicular or substantially perpendicular, to the direction x of the main path of the light 7. Thus, rotating around the first joint 13 will cause the tilt of the main path 7 on the connection 1 to vary, and rotating around the second joint 14 will cause the angle of the main path 7 with the plane of the connection 1 to vary. The motions of the joints 13 and 14 are controlled by motors 15 and 16 which they contain and which are also used for immobilizing them in desired positions. The control may be exerted by an observer or be automatic, for example if scans are undertaken.

Let us pass now to FIG. 2 for a more complete description of the system emitting and receiving light. The latter is produced by a laser 17 and conveyed in an optical fibre 19 via a fibre coupler 18. The end of the fibre 19 which is opposite to the laser 17 is fixed at the end of the arm 8, whereas the remainder of the fibre 19 and the laser 17 may be fixed. Light emerges from the optical fibre 19 in a slightly divergent beam and is sent back into the main path 7 after having crossed a pair of successive right-angle mirrors 20 and 21, and an expanding lens 22 which widens the beam and makes it parallel, and a protective glass 23. After having illuminated a portion of the connection 1 and the end of the tool 4, light reaches a second protective glass 24, and then a converging lens 25, a second pair of right-angle mirrors 26 and 27, a pinhole 28 placed at a focus of the beam made convergent by the lens 25, another lens 29 after the focus again making the beam parallel, an interferential filter or a band-pass filter 30 and a detector 31 such as an observation camera. The last mentioned means, starting from the second protective glass 24, belong to the receiver 6, whereas the first means belong to the emitter 5. As this has been seen for the emitter 5, some of the receiver means 6 may be made fixed by using optical fibre coupling. The right-angle mirrors 22, 23 and 26, 27, are not absolutely necessary but allow the emitter 5 and the receiver 6 not to be placed in alignment, with significant bulkiness along the length of the arm 8, but to be folded back against the alignment of the tubes 2 and 3, either parallel to the axis 11, as illustrated in FIG. 2, or in a vertical direction as illustrated in FIG. 3.

One of properties of this optical system is to expand the light beam emitted by the laser 17 to a relatively large section towards the main path 7 so that it illuminates all the scene to be monitored and to shrink it up to the focus of the pinhole 28, the function of which is that of a spatial filter blocking the majority of the ambient light, which will thus be unnoticed and will not perturb the perception of the shadows formed by the light of the laser. With the interferential filter or pass-band filter 30, it is possible to only retain for observation, the light rays at the wavelength emitted by the laser 17 and to again suppress a portion of the ambient light. A suitable view of the scene to be monitored is thereby obtained with these filters, even in the presence of intense ambient light produced by a molten bath or by plasma or tools raised to a high temperature by the heat sources used for welding.

Let us now pass to a description of a monitoring method.

FIG. 4 illustrates a connection profile which may be observed in the application described herein, consisting of horizontal generatrices 32 and 33 of the tubes 2 and 3, of a horizontal generatrix 34 of the connection 1 and of oblique generatrices 35 and 36 of beveled edges with a tapered shape. Parameters which one may want to measure, are the vertical distance between the horizontal generatrices 32, 33 and 34, or the horizontal distance between the generatrices 35 and 36, depending on the height, i.e., the depth or the width of the connection 1. Recognition of the profile strongly depends on the orientation of the monitoring device and especially on the optical system. In this way, the intersections of the tapered bevelled edges with planes parallel to the axis of the tubes are hyperbolas 39. As shown by the diagram of FIG. 4, the distance between the bevelled edges will be perceived with a different width L according to the orientation of the observation rays, the largest distance L (corresponding to the axial distance and which one would want to measure) appearing when the direction of observation is perpendicular to the axis of the cones. This is why it will be indicated, at least periodically, to cause oscillatory motions of the system to occur around the second joint 14, in order to adjust and re-adjust the aiming direction.

Also it is obvious that the estimation of the depth of the connection 1 depends on the tilt of the aiming direction. Especially in the case of an operation on a circular line such as the connection 1, it will be indicated to regularly subject the optical system to oscillatory motion around the first joint 13. This is particularly required in the case of a weld bead which is set back from the original surface of the connection 1, as illustrated in FIG. 5, where the upper surface of the weld bead bears the reference number 37. By maintaining a main path 7 of the light at a constant tilt, it would only be possible to measure the edge 38 of the connection 1 which overhangs the molten bath. By periodic tilt changes providing a new main path 7', it would however be possible to no longer observe the original connection 1, but the weld bead 37 itself, and to therefore provide more useful information on the condition of the welded assembly.

The laser may be replaced with another light source (notably of the LED type, a light-emitting diode). The advantage of the laser is that its light energy is concentrated in a limited spectral range so that a narrow band-pass filter may be used, which lets through the light of the laser and attenuates the parasitic illumination which covers a less wide spectrum. A power of the order of a few mW is then sufficient. Moreover an emission wavelength is selected so that the plasma is transparent for the latter. With a source characterized by a wider emission spectrum, a much larger light power is required in order to obtain the same contrast level. But low power reduces discomfort or ocular risks for an unintentional observer.

The invention claimed is:

1. A monitoring device comprising a supporting member, a light emitter, a receiver for the light emitted from the emitter, and an arm having opposite ends with the light emitter and receiver mounted at each opposite end of the arm, said monitoring device further comprising an adjustable joint connecting the arm to the supporting member to allow for rotation of the arm with respect to the supporting member about two axes of rotation (y, z) perpendicular to each other and to a main path (x) of light emitted in the form of a light beam from said emitter for illuminating a scene to be monitored with one of said two axes of rotation intersecting said light beam.

2. The monitoring device according to claim 1, wherein said main path is a part of the beam which has a greater cross-section than other parts of the beam.

3. The monitoring device according to claim 2, wherein the light is monochromatic and a filter is provided on the beam between the main path and the receiver of light, the filter being transparent to light and opaque to other optical wavelengths.

4. The monitoring device according to claim 2, comprising a converging lens provided between the main path and the receiver of light and a pinhole place at a focus of the light, said focus being created by the converging lens.

5. The monitoring device according to claim 3 comprising a converging lens provided between the filter and the receiver of light and a pinhole place at a focus of the light, said focus being created by the converging lens.

6. The monitoring device according to claim 2, comprising an expanding lens which widens the cross-section of the beam between the light emitter and the main path.

7. The monitoring device according to claim 1, wherein the support member comprises a tool separating the scene.

8. the monitoring device according to claim 1, comprising one or more motors for oscillating the arm about the two axes.

9. A method for monitoring a scene, using a monitoring device comprising a supporting member, a light emitter, a receiver of light emitted by the light emitter, an arm having opposite ends with the light emitter and receiver mounted at each opposite end of the arm and an adjustable joint connecting the arm to the support member to allow for rotation of the arm with respect to the support member about two axes of rotation, comprising the steps of:

emitting light from said emitter as a beam having a main path of light intersecting at least one of the two axes of rotation at an angle perpendicular thereto;

locating the device so that the main path is tangent to the scene; and imparting oscillations to the arm about the two axes of rotation and repeatedly measuring parameters of the scene.

10. A method according to claim 9, wherein the parameters include a width and a depth for a circular connection with the main path being tangent to the connection.

11. A method according to claim 10, wherein the aiming direction of the main path is continuously adjusted according to measurements of the parameters during the oscillations.

12. A method according to claim 10 or 11, wherein the scene is a scene of a welding connection.

\* \* \* \* \*